United States Patent [19]

Weaver

[11] Patent Number: 4,754,483
[45] Date of Patent: Jun. 28, 1988

[54] DATA COMPRESSION SYSTEM AND METHOD FOR AUDIO SIGNALS

[75] Inventor: Charles S. Weaver, Palo Alto, Calif.

[73] Assignee: SRI International, Menlo Park, Calif.

[21] Appl. No.: 89,481

[22] Filed: Aug. 25, 1987

Related U.S. Application Data

[63] Continuation of Ser. No. 560,610, Dec. 12, 1983, abandoned, which is a continuation-in-part of Ser. No. 202,457, Oct. 31, 1980, Pat. No. 4,449,536.

[51] Int. Cl.⁴ ............................ G10L 5/00; G11B 5/09
[52] U.S. Cl. ......................................... 381/36; 360/51
[58] Field of Search .................... 381/29, 31; 128/696; 364/415, 417, 724; 333/166; 360/51

[56] References Cited

U.S. PATENT DOCUMENTS

| | | | |
|---|---|---|---|
| 3,598,921 | 8/1971 | Paine | 381/31 |
| 4,413,289 | 11/1983 | Weaver et al. | 381/31 |
| 4,534,055 | 8/1985 | Iinuma | 381/34 |

OTHER PUBLICATIONS

Bertrand et al, "Microprocessor Application . . . ", Proc. IEEE, May, 1977, pp. 714-722.

Ruttiman et al, "Compression of the ECG . . . ", IEEE Trans. Biomed. Eng., Nov. 1979, pp. 613-623.

Ripley et al, "A Computer System . . . ", Biomed. Lab., Washington U. (MO), 1976, pp. 439-445.

*Primary Examiner*—Emanuel S. Kemeny
*Attorney, Agent, or Firm*—Victor R. Beckman

[57] ABSTRACT

A data reduction system is disclosed which includes an analog to digital converter for converting an analog signal to digital sample signal form, a digital compression filter for compression filtering the digital sample signals, and an encoder for truncated Huffman encoding the compression filter output. A decoder for decoding the encoded signal, a digital reconstruction filter for decomposition filtering of the decoded signal, and digital to analog converter means are included to reconstruct the analog signal. The digital compression filter has a transfer function which includes zeros as the unit circle in the Z-plane, while the digital reconstruction filter has poles that normally are on or inside the unit circle in the Z-plane at the same angular positions as the zeros of the digital compression filter. The poles of the reconstruction filter are momentarily movable inwardly from their normal positions in response to a detected error signal to speed recovery from such error signal.

11 Claims, 6 Drawing Sheets

FIG-2

A] ANALOG INPUT

B] A/D CONVERTER 20 OUTPUT: $f_{n-1}$ (14 BITS), $f_n$ (14 BITS), $f_{n+1}$ (14 BITS), ..., $f_{n+i}$ (14 BITS)

C] COMPRESSION FILTER-30 OUTPUT W/O TRUNCATION: $\Delta_n$ (18 BITS), $\Delta_{n+1}$ (18 BITS), $\Delta_{n+2}$ (18 BITS), ..., $\Delta_{n+i}$ (18 BITS)

D] ENCODER-40 OUTPUT: $h(\Delta_n)$ (1 TO 24 BITS), $h(\Delta_{n+1})$ (1 TO 24 BITS), $h(\Delta_{n+2})$ (1 TO 24 BITS), ..., $h(\Delta_{n+i})$ (1 TO 24 BITS)

E] DECODER-66 OUTPUT: $\Delta_n$ (18 BITS), $\Delta_{n+1}$ (18 BITS), $\Delta_{n+2}$ (18 BITS), ..., $\Delta_{n+i}$ (18 BITS)

F] RECONSTRUCTION FILTER-70 OUTPUT WITH ARITHMETIC WORD LENGTH TRUNCATION: $f_n(out)$ (24 BITS), $f_{n+1}(out)$ (24 BITS), $f_{n+2}(out)$ (24 BITS), ..., $f_{n+i}(out)$ (24 BITS)

DATA COMPRESSION SYSTEM AND METHOD FOR AUDIO SIGNALS

RELATED APPLICATIONS

This is a continuation application of U.S. patent application Ser. No. 560,610 filed Dec. 12, 1983 by Charles S. Weaver, abandoned, which, in turn, is a continuation-in-part application of U.S. patent application Ser. No. 202,457 filed Oct. 31, 1980 by Charles S. Weaver, entitled Method and Apparatus for Digital Data Compression, now U.S. Pat. No. 4,449,536, issued May 22, 1984.

BACKGROUND OF THE INVENTION

Systems which include means for converting analog signals to digital form, then compression filtering and Huffman encoding the signals for recording or for transmission to a remote location, together with playback or receiver means which include a Huffman decoder, a digital reconstruction filter and means for converting the decoded and filtered digital signals back to analog form are shown in the above-identified U.S. patent application Ser. No. 202,457, and in an article by U. E. Ruttimann and H. V. Pipberger entitled, "Compression of the ECG by Prediction or Interpolation and Entropy Encoding", *IEE Transactions on Biomedical Engineering*, Vol. BME-26, No. 11, pp. 613–623, Nov. 1979. A similar system is shown in an article by K. L. Ripley and J. R. Cox, Jr. entitled, "A Computer System for Capturing Transient Electrocardiographic Data", *Pro. Comput. Cardiol.* pp. 439–445, 1976. With the present invention, the average bit rate of an analog-to-digital converted audio signal, such as a music, electrocardiogram, or electroencephalogram signal, is reduced sufficiently to allow for digital transmission thereof over low-grade transmission lines and/or recording and playback of a worthwhile quantity of signal using a relatively small amount of recording medium and employing known digital recording and playback techniques.

SUMMARY OF THE INVENTION

Audio signal, such as music, to be transmitted, or recorded, are converted to digital form by analog to digital converter means. The digital signals then are supplied to a digital compression filter to generate digital, compressed signals. The compressed audio signals are supplied to an encoder, such as a truncated Huffman encoder, for encoding the same. The digital output from the encoder is recorded by use of digital recording means, and/or transmitted to a remote receiving location. At a playback unit or receiving station the encoded signal is decoded by a decoder, and the decoded signal is supplied to a digital decompression filter. The output from the decompression filter is converted to analog form by digital to analog converter means to provide a reproduction of the audio signals.

An unstable compression-decompression filter combination results when the decompression filter transfer function includes poles on the unit circle of the Z-plane. In accordance with the present invention, transfer of the output from the Huffman encoder includes use of an error-checking code and error detecting means for detection of errors in said transfer to the Huffman decoder. An error signal is produced in response to the detection of an error in such digital signal transfer, which error signal is supplied to the decompression filter for use in momentarily moving the poles of said filter inwardly, inside the unit circle thereby enabling the system to recover from said signal errors.

Also, in accordance with the present invention, the above-described error signal detection and inward movement of the poles of the transfer function in the Z-plane of the decompression filter in response to error detection also may be used in those systems having stable compression-decompression filter combinations to accelerate recovery from signal errors.

BRIEF DESCRIPTION OF THE DRAWINGS

The invention will be better understood from the following description when considered with the accompanying drawings. In the drawings, wherein like reference characters refer to the same parts in the several views:

FIG. 2, consisting of A–F, shows a waveform and graphic representations of signals appearing at various locations in the data compression system shown in FIGS. 1A and 1B;

Figure 1A:
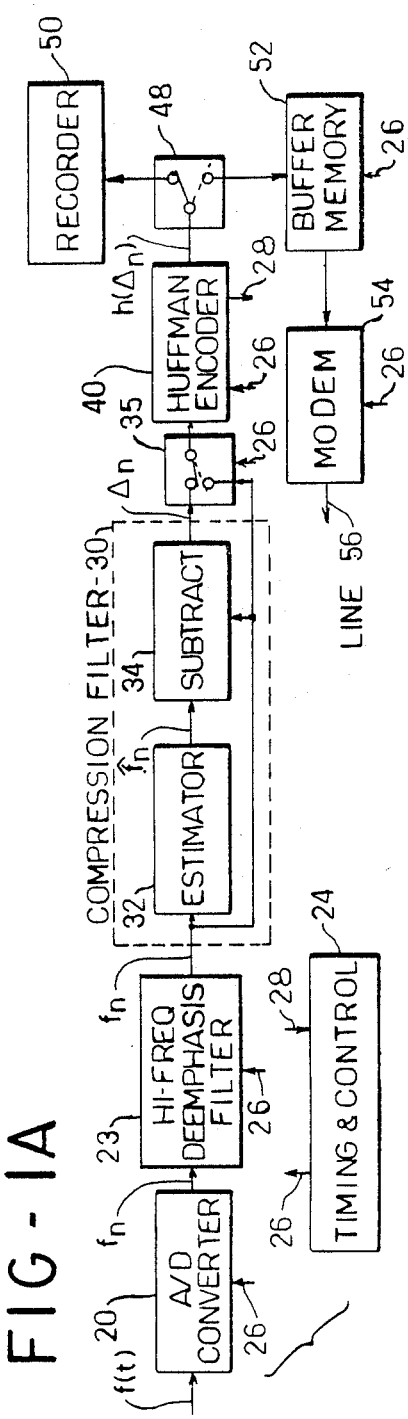
FIGS. 1A and 1B together show a block diagram of a data reduction system; a digital recording and transmitter section being shown in FIG. 1A and a playback and receiver section being shown in FIG. 1B.

The invention in the present application specifically is illustrated in FIGS. 7A and 7B through FIG. 10, described hereinbelow. However, for a better understanding of the invention, a brief description of FIGS. 1A and 1B through FIG. 6 first is provided. Reference first is made to FIG. 1A wherein the digital recording and transmitting portion of a data compression system is shown comprising an analog to digital converter (A/D converter) 20 for conversion of an analog audio signal f(t) into digital form, the $n^{th}$ sample from the analog to digital converter 20 being identified as $f_n$. At A of FIG. 2, an analog signal 22 is shown which comprises an input to the analog to digital converter 20. For purposes of illustration, the audio input signal may comprise a music signal which ranges in frequency from approximately 15 to 20,000 Hz. The form of the analog to digital converter output, shown at B of FIG. 2, comprises samples $f_{n-1}$ through $f_{n+i}$ of equal length words. The analog to digital converter 20 operates at a sampling rate established by control signals from a timing and control unit 24 supplied thereto over timing line 26. As employed herein, line 26 from the timing and control unit 24 represents a plurality of timing circuit outputs, one or more of which are supplied to the system elements for proper system timing and control. Inputs also are supplied to the timing and control unit over line 28 for control thereof by signals from various other system elements. The A/D converter 20 operates in a conventional manner at a fixed sampling rate and with a fixed word length output. For purposes of description only, and not by way of limitation, the A/D converter may operate at a sampling rate of 44 KHz and with a 14 bit word length.

Figure 2A:
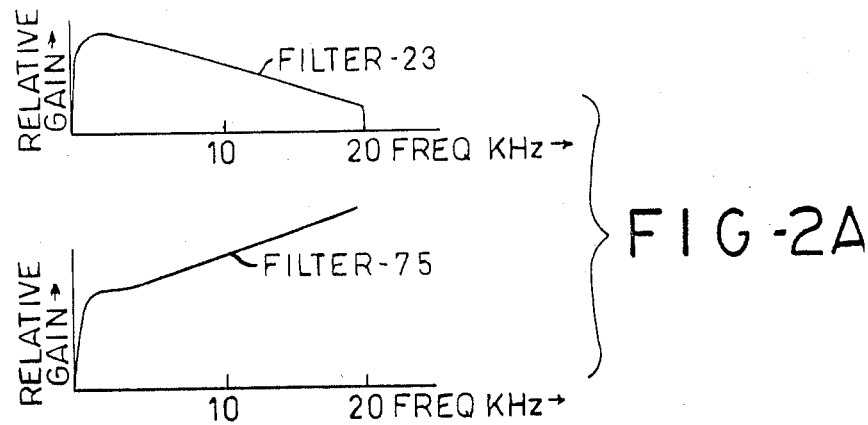
FIG. 2A shows the frequency response of high frequency deemphasis and high frequency emphasis filters which are included adjacent the input and output, respectively, of the data reduction system.
Figure 3:
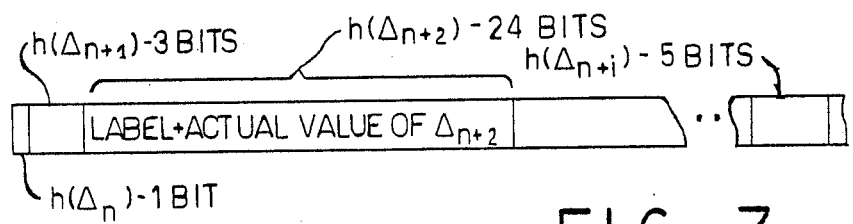
FIG. 3 is a graphic representation of encoded difference signals showing the format employed for encoding those difference signals which are outside a predetermined signal range.

The output from the A/D converter 20 is supplied to a digital compression filter 30 through a digital filter 23 which deemphasizes the high frequency portion of the digital audio frequency signal from the A/D converter 20 to reduce the signal entropy. The frequency response of filter 23, together with the frequency response of a digital filter 75 included in the playback and receiver portion of the system is shown in FIG. 2A. For simplicity, the digital output from filter 23, as well as the digital input, is identified as $f_n$. Obviously, an analog filter having a similar frequency response may be included at the input to the A/D converter 20 in place of the digital filter 23 at the output therefrom.

For present purposes, the digital compression filter 30 is shown to include an estimator 32 and subtracting means 34. The estimator 32 provides an estimate of $f_n$, here identified as $\hat{f}_n$, based upon actual samples occurring both before and after the sample $f_n$ to be estimated. Estimators for providing such estimated $\hat{f}_n$ values are, of course, well known. A difference signal $\Delta_n$ is produced by the compression filter 30 comprising the difference between the actual signal input $f_n$ and the estimated signal value $\hat{f}_n$ by subtraction of the estimated value from the actual value at subtracting means 34, as follows:

$$\Delta_n = f_n - \hat{f}_n \tag{1}$$

In the graphic signal representation of the compression filter output shown at C in FIG. 2, difference signals $\Delta_n, \Delta_{n+1}, \Delta_{n+2}, \ldots \Delta_{n+i}$ are shown. In accordance with one feature of this invention, arithmetic operations of the digital compression filter 30 are performed without truncation or round-off whereas arithmetic operations of an associated digital decompression, or reconstruction filter, described below, are performed with truncation, or round-off. As seen in FIG. 2C, the compression filter output comprises untruncated compressed signals which are 18 bits in length.

It here will be understood that the present invention is not limited to use with the illustrated compression filter in which the output $\Delta_n$ comprises the difference between the actual signal input $f_n$ and an estimated value $\hat{f}_n$. Other compression filters may be used having different transforms in which the compression filter output $\Delta_n$ is not a direct function of the difference between the actual input $f_n$ and an estimated value thereof, $\hat{f}_n$. The use of the term "difference" signal values $\Delta_n$ is intended to also identify the output from other suitable compression filters.

The compressed signal values $\Delta_n$ are supplied, through switch 35, to an encoder 40 employing a truncated Huffman code for encoding the same. Huffman encoding is disclosed in copending U.S. patent application Ser. No. 207,728, filed Nov. 17, 1980, entitled "Method and Apparatus for digital Huffman Encoding" by Charles S. Weaver, now U.S. Pat. No. 4,396,906, issued Aug. 2, 1983, which application is assigned to the same assignee as the present invention. The entire disclosure of said U.S. patent application Ser. No. 207,728 specifically is incorporated by reference herein. Briefly, the Huffman encoding technique makes use of the fact that the compression filter reduces the entropy of the signal output, $\Delta_n$ so that there can be a reduction in the total number of bits in the Huffman encoded signal over the input signal. A single code word is assigned to infrequently occurring difference signals, and supplied as a label for the actual difference signal value $\Delta_n$. In FIG. 1A, the encoder 40 output is designated $h(\Delta_n)$ and, at D in FIG. 2, the values $h(\Delta_n)$, $h(\Delta_{n+1})$ etc. represent encoded values of $\Delta_n$, $\Delta_{n+1}$, etc. the most frequently occurring value of $\Delta_n$ (here zero) is encoded using the shortest code word. A truncated Huffman code is disclosed in U.S. patent application Ser. No. 207,728 which is readily implemented using a simple encoder and decoder. The encoder 40 output comprises code words for the most frequently occurring values of $\Delta_n$, together with a combined code word label and actual value of the compressed signal $\Delta_n$ for less frequently occurring values of $\Delta_n$. For purposes of illustration, if the compressed signal value exceeds $\pm 3$ then the actual compressed signal $\Delta_n$ together with a code word label is produced at the encoder output. At FIG. 3, wherein several encoded compressed values are shown, it will be seen that the encoded value for $\Delta_{n+2}$ comprises a label together with the actual compressed signal $\Delta_{n+2}$, wherein $\Delta_{n+2}$ comprises an infrequently occurring compressed signal value; that is, some value outside the range of $\pm 3$.

The encoded signals from encoder 40 are recorded and/or transmitted to a remote receiver. For recording, the encoder output is connected through a switch 48 to a recording unit 50 for recording of the encoded difference signals, labeled $h(\Delta_n)$ signals. With the switch 48 in the other, broken line, position, the encoder output is supplied to a buffer memory 52 and thence to a digital modem 54 for transmission over transmission line 56. In accordance with the present invention, described hereinbelow, check bits are generated for recording and/or transmitting along with encoded compressed signals $h(\Delta_n)$. Also, digital input signals $f_n$ sometimes may be supplied to the input of the Huffman encoder through switch means 35, which signals serve to initialize, or reinitialize, the associated digital reconstruction filter described below.

Figure 1B:
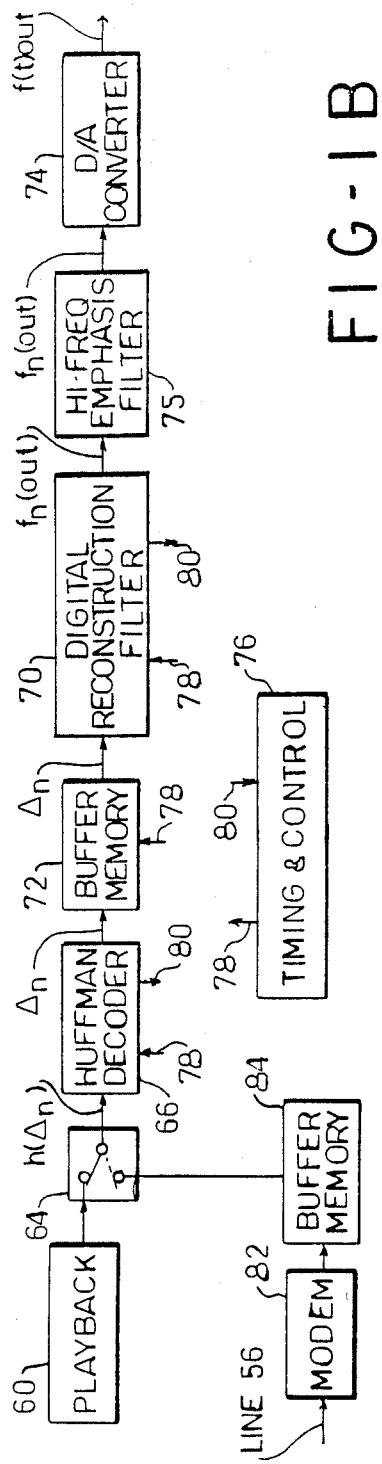

Recorded encoded digital signals, such as those recorded at recording unit 50 of FIG. 1A are reproduced using the system shown in FIG. 1B, which system includes a playback unit 60. Recorded encoded digital signals from the playback unit 60 are supplied through switch 64 to a decoder 66 for decoding the truncated Huffman encoded signals. At the decoder 66, the Huffman code words are converted to the original compressed signals $\Delta_n$. Where the Huffman code word comprises a labeled actual compressed signal, the label is stripped therefrom, and the actual compressed signal without the label is supplied to the decoder output. Encoding and decoding means which may be used in the present invention are described in detail in the above-mentioned copending U.S. patent application Ser. No. 207,728.

The compressed signals $\Delta_n$ from the decoder 66 are supplied to a reconstruction, or decompression, filter 70 through a buffer memory 72. The decoder output signals are produced at slightly varying rates, and the buffer memory 72 is included to accommodate the input rate requirements of the reconstruction filter 70. The reconstruction filter 70 converts the compressed signals $\Delta_n$ to equal length sample signals $f_n(\text{out})$ which closely match the input sample signals $f_n$ to the compression filter 30. Compression filtering is without truncation and decompression filtering is with truncation during operation of the reconstruction filter while the filter poles are inside the unit circle in the Z-plane. In FIG. 2F, the truncated reconstruction filter output $f_n(\text{out})$, $f_{n+1}(\text{out})$ etc. is shown to comprise words of 24 bits. Without truncation, the reconstruction filter would be required to handle word lengths of approximately 36 to 40 bits which, for consumer products, is not now feasible at reasonable cost. Suitable data compression with minimum distortion is obtained using a compression-decompression filter combination wherein compression filtering is effected without truncation and decompression filtering is effected with truncation.

A digital to analog converter (D/A converter) 74 converts the signal samples $f_n(\text{out})$ from the digital reconstruction filter 70 to analog form, for reproduction of the analog signals. A digital filter 75 which emphasizes the high frequency components of the signal output is included in the connection of the output from the digital reconstruction filter output to the D/A converter. The frequency response of the filter 75 is shown in FIG. 2A, adjacent the frequency response of the input filter 23. For simplicity, the same symbol $f_n(\text{out})$ is employed at the input and output of the filter 75. Obviously, an analog filter having a similar frequency response may be included in the output from the D/A converter, in place of the digital filter 75. A receiver timing and control unit 76 supplies timing signals to the various receiver elements over line 78 for proper timing of the receiving operation. Also, control signals for the unit 76 are supplied thereto over line 80 from various elements of the receiver for control thereof.

For transmission without recording, the encoded signals are transmitted over line 56 (from FIG. 1A to FIG. 1B) to a digital modem 82 at the reciever. The modem output is buffered by buffer memory 84, and the buffer memory output is supplied through switch 64 in the broken line position to the decoder 66 for decoding and subsequent processing in the manner described above.

COMPRESSION FILTERING OF QUANTIZED MUSIC SIGNALS

The compression filter may implement, for example, the following equation.

$$\Delta_n = f_n - 2f_{n-1} + f_{n-2} \quad (2)$$

The Z-transform of Eq (2) is $$G(Z) = (1 - 2z^{-1} + z^{-2}) = (1 - z^{-1})^2 \quad (3)$$

which can be represented by two zeros at (1,0) in the Z-plane. Other angular zero positions may be used for compression filtering including, for example, $\pm 41.41°$, $\pm 60°$, $\pm 90°$, $\pm 120°$ and $180°$.

COMPRESSION FILTER

Figure 4:
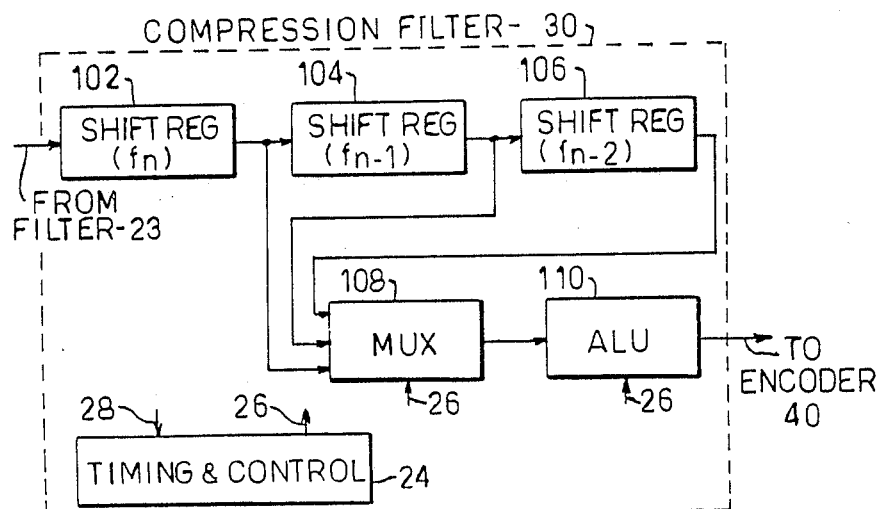
FIG. 4 is a block diagram showing details of a compression filter of the type which may be used in the present system.

Although it will be apparent that standard digital techniques may be used for implementing compression filter transforms, including the use of a programmed digital computer, a block diagram of a second order digital compression filter suitable for use in implementing equation (2) is shown at FIG. 4, to which figure reference now is made. The illustrated compression filter includes a series of shift registers 102, 104, and 106 into which consecutive sample signals from the A/D converter, through filter 23, are shifted. In FIG. 4, for purposes of description, the registers, 102, 104 and 106 are shown to contain samples $f_n$, $f_{n-1}$, $f_{n-2}$, respectively. For 14-bit samples, 14-bit registers are employed. The register outputs are connected to a digital multiplexer 108 for selective connection of the sample signals to an arithmetic and logic unit (ALU) 110. The multiplexer 108 and ALU 110 are under control of timing and control unit 24.

As noted above in the description of FIG. 1A, the digital compression filter 30 may include an estimator 32 having an output comprising an estimated sample value $\hat{f}_n$ based upon actual samples $f_{n-1}$ and $f_{n+1}$ occurring before and after the sample $f_n$ to be estimated. Often, prior art estimators are used which provide an output, $$\hat{f}_n = a_1 f_{n+1} + a_2 f_{n-1} \quad (4)$$

where the coefficients $a_1$ and $a_2$ are chosen to minimize the mean square error of the difference $\Delta_n$, where $\Delta_n = f_n - \hat{f}_n$, as noted in equation (1), above. For $a_1 = a_2 = 1$, equations (1) and (4) may be combined to give $$\Delta_n = f_{n+1} - 2f_n + f_{n-1} \quad (5)$$

(It here will be noted that equations (2) and (5) are equivalent.)

Equation (5) may be utilized by the illustrated compression filter in the generation of the compressed signal $\Delta_n$. An estimate $\hat{f}_n$ of the sample $f_n$ is made using the samples either side of $f_n$, i.e. $f_{n-1}$ and $f_{n+1}$, but not $f_n$ itself. Under control of unit 24, the words $f_{n-1}$ and $f_{n+1}$ are moved into the ALU 110 through the multiplexer 108 and added. The actual sample $f_n$ then is moved into the ALU 110 through the multiplexer 108, and multiplied by 2. Multiplying by 2 simply involves shifting of the bits toward the most significant bit. The actual sample $f_n$, multiplied by 2, is subtracted from $f_n$ to provide the compressed signal value $\Delta_n$ at the ALU 110 output, which then is supplied to encoder 40. The arithmetic in the ALU 110 is done in a word length sufficiently long to ensure against truncation or round-off error. It will be seen that data compression by the above-described apparatus includes estimating a sample value by interpolation.

HUFFMAN ENCODING AND DECODING

As noted above, Huffman encoding and decoding means suitable for use in the present system for encoding and then decoding the compression filter output are disclosed in copending U.S. patent application Ser. No. 207,728 filed Nov. 17, 1980, now U.S. Pat. No.

4,396,906, entitled, "Method and Apparatus for Digital Huffman Encoding" by the present inventor, which application is incorporated by reference herein.

RECONSTRUCTION FILTERING

Entropy Versus Reconstruction Filter Stability

For exact reconstruction of the digital music signal supplied to the digital compression filter 30, the reconstruction filter 70 transfer function would have to be the inverse of the compression filter 30 transfer function. (Two other necessary conditions for exact reconstruction are that there be no over- or under-flow errors in the filter arithmetic and that there be no truncation of the compression filter output word length.)

Minimum entropy is obtained when the zeros of the compression filter transfer function are on the unit circle. The exact inverse has poles on the unit circle in the same positions as the compression filter zeros. Such a reconstruction filter is unstable. Such instability is satisfactory until a bit error occurs whereupon incorrect, and random, "initial conditions" cause the reconstruction filter to diverge to saturation. The present invention is adapted for use with arrangements wherein the compression-reconstruction filter combination either is normally stable or normally unstable.

In either case, the novel system includes the use of check bits and error checking means for production of a bit error signal whenever an error is detected. The error signal is used to momentarily move the poles of the reconstruction filter 70 inwardly of the unit circle, during which time the filter 70 recovers from errors without the need to reinitialize the filter with actual signal values $f_n$. By locating the poles of the reconstruction filter inside the unit circle, the filter is stable and incorrect "initial conditions", due to errors, will damp out. Under these conditions, the filter is stable and no blocking is required for recovery from errors. Stable filter combinations of this type also are described in further detail hereinbelow.

Reconstruction Filter Not an Exact Inverse of Compression Filter

Figure 5:
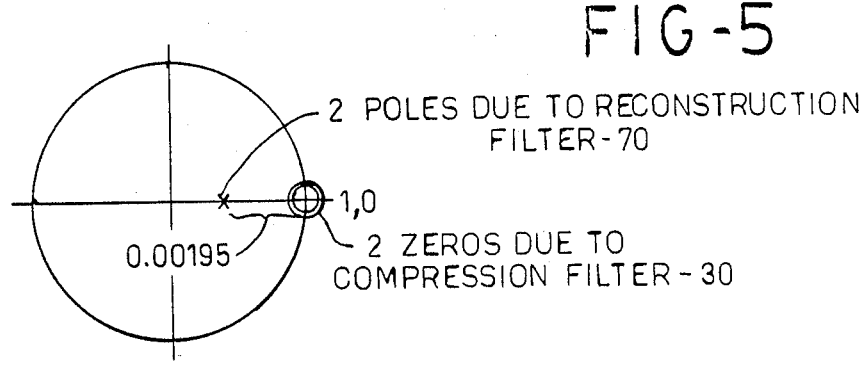
FIG. 5 shows the zero-pole pattern of a compression-reconstruction filter combination which results in a stable system.
Figure 6:
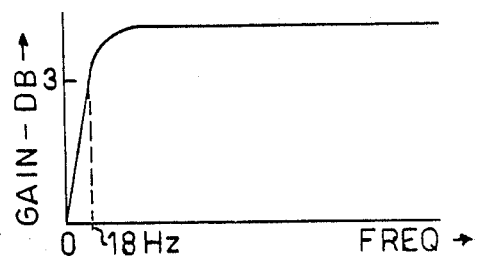
FIG. 6 shows the frequency response of the compression-reconstruction filter combination having the zero-pole pattern illustrated in FIG. 5.

If there are no bit errors in the transfer of the compression filter 30 output to the input of the digital reconstruction filter, and no truncation of the compression filter 30 output, the output from the Huffman decoder 66 is identical to the output from the compression filter 30. Thus, it will be understood that the transfer from the input to the compression filter 30 to the output of the reconstruction filter 70 is simply the product of the transforms of the two filters 30 and 70. The data compression system shown in FIGS. 1A and 1B may include, for example a compression-reconstruction filter combination wherein the zeros of the compression filter are at specific points on the unit circle to reduce the entropy, and corresponding poles of the reconstruction filter are located inside the unit circle, adjacent said zeros for stability. The frequency response and stability of such compression-reconstruction filter combinations are readily calculated. Consider, for example, a compression-reconstruction filter combination wherein the compression filter has two zeros at (1,0) and the reconstruction filter has two poles at (1−0.00195, 0). The pole-zero pattern of such a compression filter cascaded with a reconstruction filter is shown in FIG. 5, and the frequency response of the filter combination is shown in FIG. 6. As seen in FIG. 6, the combination provides a very flat high-pass filter with a 18 Hz cut-off. With this filter combination, recovery from bit errors is within 20–30 ms. It here will be noted that the reconstruction filter 70 employed herein preferably comprises a digital computer programmed for the desired reconstruction filter operation.

Word Length Considerations in the Reconstruction Filter

A stable reconstruction filter, operating without truncation, would require a large arithmetic word length. For example, the above-described-real-pole 18 HZ filter would require at least 34 bit arithmetic ($0.00195 = 2^{-9}$), at least 9 bits per pole on the least significant end and 1 bit on the most significant end per pole when the analog to digital (A/D) word length is 14 bits. 4-pole configurations would require even longer arithmetic word length. Presently, computers operating with such large word lengths are not practical for consumer music data compression.

Fortunately, the reconstruction filter arithmetic words can be truncated to practical lengths with negligible system degradation.

SYSTEM OF THIS INVENTION WITH ERROR DETECTION AND MOVABLE RECONSTRUCTION FILTER POLES

Figure 7A:
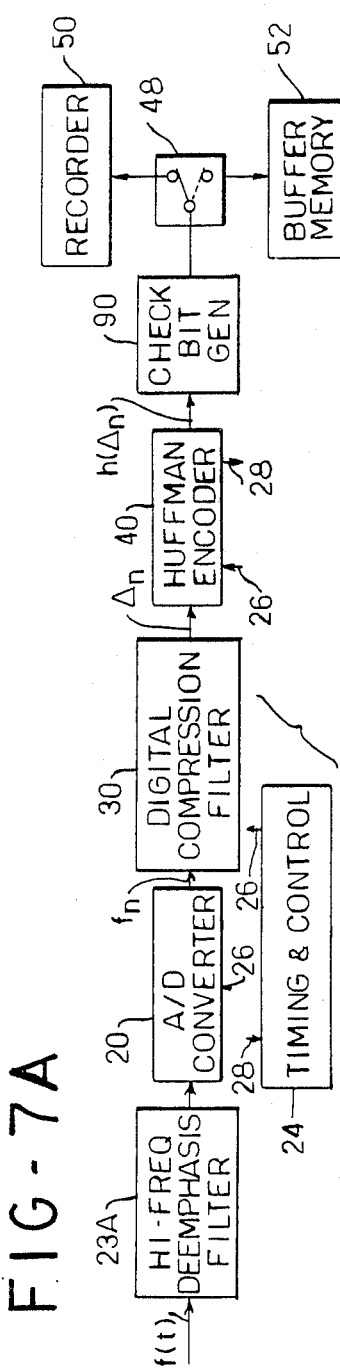
FIGS. 7A and 7B are similar to FIGS. 1A and 1B, respectively, but showing a novel system which includes a check bit generator and error checking means for use in momentarily moving the poles of the reconstruction filter inwardly when a bit error is detected.
Figure 7B:
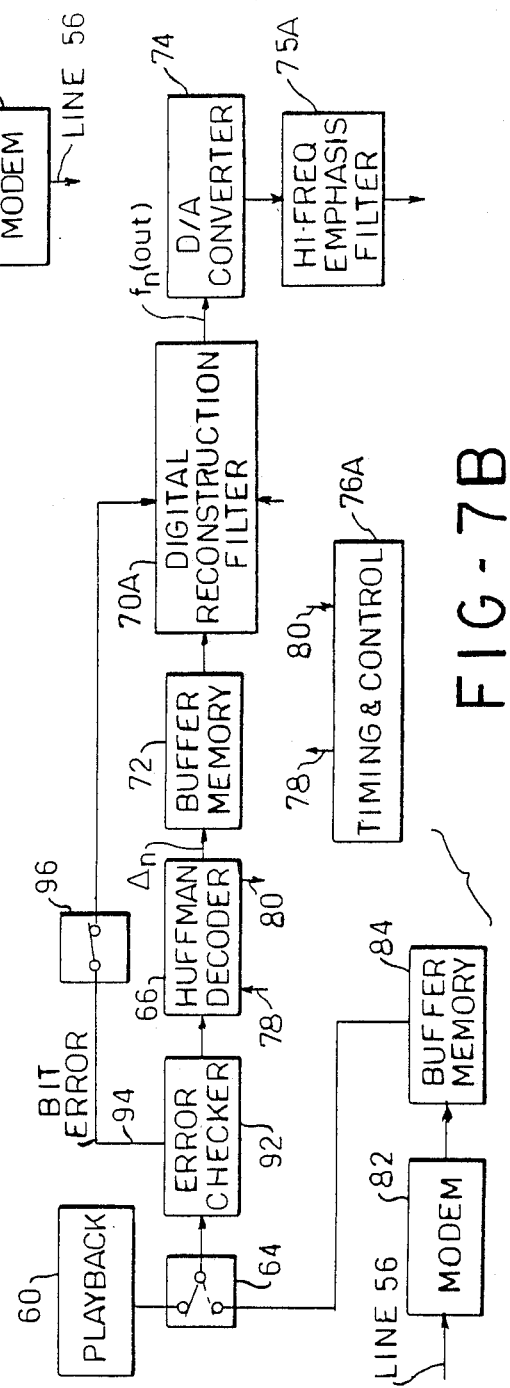

In FIGS. 7A and 7B one form of this invention is shown wherein check bits are generated for recording and/or transmitting along with the encoded digital compressed signals. At the playback and/or receiver unit, any errors detected using the check bits serve to generate an error signal which is used to momentarily move the poles of the digital reconstruction filter inwardly, or further inwardly, of the unit circle in the z-plane without changing the pole angle. For an unstable reconstruction filter, momentary movement of the poles inwardly of the unit circle results in a stable filter combination which recovers from playback and/or transmission errors without the need for reinitialization of the filter. For a stable reconstruction filter, momentary movement of the poles inwardly of the unit circle provides for accelerated recovery from error signals.

Reference first is made to FIG. 7A wherein the digital recording and transmitting portion of a modified form of data compression system which includes the use of check bits is shown. The system of FIG. 7A is similar to that of FIG. 1A and is shown to include an analog to digital converter 20, digital compression filter 30, Huffman encoder 40, switch 48, recorder 50, buffer memory 52, modem 54 and timing and control unit 24, all of which may be of the same type as shown in FIG. 1A and described above. It will be noted that an analog high frequency deemphasis filter 23A is included in the input of the A/D converter which filter serves the same function as digital filter 23 shown in FIG. 1A.

In the form of invention shown in FIG. 7A, a check bit generator 90 is shown included in the connection of the Huffman encoded signal $h(\Delta_n)$ to the recorder 50 or modem 54, dependent upon the position of switch 48. Check bits generated by check bit generator 90 are added to the digital stream of Huffman encoded signals for recording and/or transmission along with said encoded digital compressed signals. Numerous schemes for the generation of check bits, and for error detection using such check bits are well known and require no detailed description. It here will be noted that recorders and modems often include check bit generator means for the generation of check bits to be added to the data stream to be recorded, or transmitted.

Recorded encoded digital signals, with check bits, such as those recorded at recorder 50, are reproduced using playback unit 60 shown in FIG. 7B, to which figure reference now is made. Signals transmitted by modem 54 (FIG. 7A) are transmitted over line 56 to modem 82 (FIG. 7B). Switch 64 connects the playback output, or modem output, to an error checking circuit 92 where the signal stream is checked for bit errors. When an error is detected, a bit error signal is generated which signal is transmitted over line 94 and through switch 96 to the digital reconstruction filter for momentarily shifting the poles of the filter inwardly.

Check bit signals are stripped from the signals from the playback unit 60 and/or modem 82 by the error checking means 92, and the Huffman encoded digital compressed signal stream $h(\Delta_n)$ from the error checker is supplied to the Huffman decoder 66, which decoder may be of the same type as shown in FIG. 1B and described above. From the Huffman decoder, the digital compressed signals $\Delta_n$ are supplied through buffer memory 72 to the digital reconstruction filter 70A. As with reconstruction filter 70 of FIG. 1B, the reconstruction filter 70A operates with truncation and converts the compressed signal input $\Delta_n$ thereto to equal length sample signals $f_n(out)$ which closely match the input sample signals $f_n$ to the compression filter 30 (FIG. 7A). A digital to analog converter 74 converts the signal samples $f_n(out)$ to analog form, f(t) out. An analog high frequency emphasis filter 75A is included at the output of the D/A converter, which filter serves the same function as filter 75 in FIG. 1B; i.e. to restore the amplitude of the high frequency signals which were deemphasized by filter 23A.

Poles Inside Unit Circle in Z-plane

As noted above, one embodiment of the present invention includes the use of a compression-reconstruction filter combination wherein the zeros of the compression filter are on the unit circle, and the reconstruction filter has corresponding poles inside the unit circle, adjacent said zeros which provide for stable operation. Recovery of the reconstruction filter from bit errors is accelerated by momentarily moving the poles of the reconstruction filter inwardly of the unit circle in the Z-plane whenever an error signal is produced by error checker 92.

Figure 8:
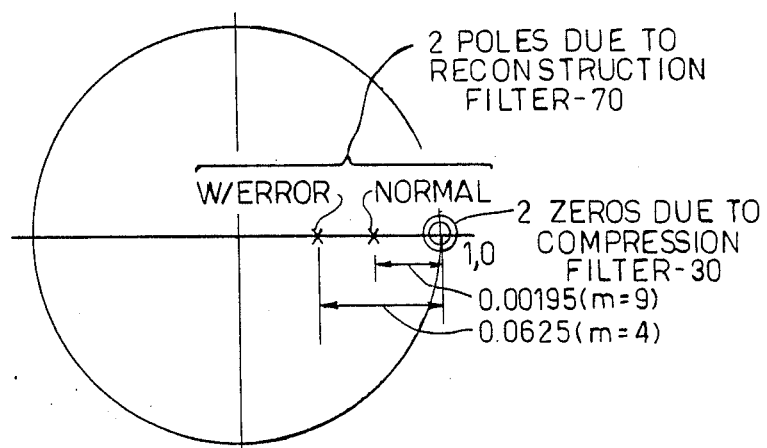
FIG. 8 shows a zero-pole pattern of a compression-reconstruction filter combination in which poles of the reconstruction filter are momentarily moved inwardly to accelerate recovery from transients.

Reference is made to FIG. 8 wherein zeros and poles of the transfer function of a compression-reconstruction filter combination are shown. The compression filter zeros are shown on the unit circle at zero degrees, and a pair of reconstruction filter poles are shown adjacent the zeros and normally at a distance of 0.00195 inside the unit circle. It will be noted that this combination of zeros and poles is the same as that shown in FIG. 5, described above. However, in the system illustrated in FIG. 8, the reconstruction filter poles are momentarily moved inwardly upon receipt of a bit error signal from the error checker 92 over line 94. For purposes of illustration, the poles are shown moved to a point 0.0625 inside the unit circle for rapid recovery from the error. After a short period of time, say 50 ms, the poles of the reconstruction filter return to normal position, that is, to a point 0.00195 inside the unit circle at zero degrees.

Difference equations for a reconstruction filter having two poles at 0° and inside the unit circle are:

$$y_n = \Delta_n + ay_{n-1} = \Delta_n + y_{n-1} - 2^{-m}y_{n-1} \quad (6)$$

$$f_n = y_n + af_{n-1} = y_n + f_{n-1} - 2^{-m}f_{n-1} \quad (7)$$

where:
$a = 1 - 2^{-m}$ and
m = an integer.

Figure 9:
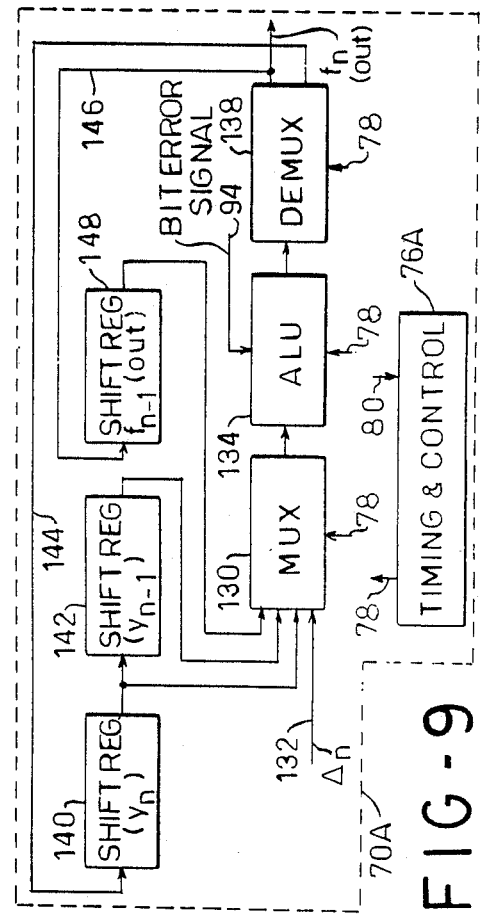
FIG. 9 is a block diagram showing details of a reconstruction filter which may be used in this invention.

A reconstruction filter for implementing equations (6) and (7) is shown in FIG. 9, to which figure reference now is made. The illustrated reconstruction filter 70A, comprises a 4 to 1 digital multiplexer 130 having one input 132 to which compressed signals $\Delta_n$ are supplied from the decoder 66. The output from the multiplexer 130 is supplied to an arithmetic and logic unit, ALU, 134 where the required multiplication by shifting, addition and subtraction take place under control of timing and control unit 76A.

The output from ALU 134 is connected to the input of a 1 to 2 digital demultiplexer 138. One output of the demultiplexer 138 is connected to one register of a pair of series connected shift registers 140 and 142 over line 144. The other demultiplexer output is connected over line 146 to a single shift register 148. The value of $y_n$ determined by the ALU is loaded into register 140 while the prior value of $y_n$ is shifted from register 140 into register 142. The third register 148 is supplied with the sample value $f_n(out)$ as calculated by the ALU 134.

Outputs from registers 140, 142, and 148 are supplied as inputs to the ALU 134 through the multiplexer 130. When used, the value stored in register 148 comprises $f_{n-1}(out)$. From equation (6) it will be seen that the value $y_n$ is calculated using the $\Delta_n$ and $y_{n-1}$ inputs to ALU 134 available at line 132 and from register 142. From equation (7) it will be seen that the sample value $f_n(out)$ is calculated using the $y_n$ and $f_{n-1}(out)$ inputs from registers 140 and 148, respectively.

So long as m equals an integer less than infinity, the reconstruction filter 70A operates stably, and neither intialization nor reinitialization of the filter is required. In the absence of bit errors the filter is operated with a relatively large value of m, say m=9, to place the poles of the filter adjacent the unit circle at 0.00195 from the unit circle. When an error is detected by error checker 92, a smaller value of m is used, say m=4, thereby moving the poles of the filter inwardly to a point 0.0625 from the unit circle. The bit error signal from error checker 92 (FIG. 7B), which is supplied to the ALU 134 over line 94, controls the value of m used in the implementation of equations (6) and (7) simply by controlling the amount of shifting to perform the indicated multiplications by the factor $2^{-m}$. When an error is detected, contents of an ALU register are not shifted as far to the right for some nominal length of time (say 50 ms) when performing the multipications by $2^{-m}$, thereby moving the reconstruction filter poles inwardly away from the unit circle to accelerate recovery from transients. After this short time period, operation returns to normal with the reconstruction filter poles again adjacent the unit circle.

Poles Normally on Unit Circle in Z-plane

Figure 10:
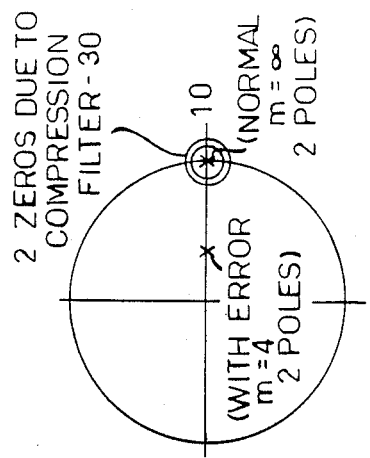
FIG. 10 shows the zero-pole pattern of another compression-reconstruction filter combination which may be used in systems embodying the present invention.

As noted above, another embodiment of the present invention involves use of a compression-reconstruction filter combination wherein the zeros of the compression filter are on the unit circle and the reconstruction filter has corresponding poles which also are on the unit circle at the same locations as the zeros, during normal operation; that is during operation in the absence of bit errors. However, when a bit error is sensed by error checker 92, the poles of the reconstruction filter 70A are momentarily moved inwardly of the unit circle for stable reconstruction filter operation, and recovery from the error. This embodiment may be implemented using the above-described receiving, or playback, unit shown in FIG. 7B, and reconstruction filter 70A shown in FIG. 9. Now, however, the reconstruction filter 70A, in the absence of transients, operates with poles on the unit circle, as shown in FIG. 10. In FIG. 10, two zeros of the compression filter 30 are shown located on the unit circle in the Z-plane at zero degrees, and, during operation in the absence of bit errors, the two poles of the reconstruction filter 70A are located at the same point on the unit circle, at a point where m equals infinity.

In the presence of a bit error signal from error checker 92, the reconstruction filter poles are momentarily moved inwardly, of the unit circle, at zero degrees. For purposes of illustration, the value of m is shown changed to 4. Under these conditions, the reconstruction filter quickly recovers from the error without the need for initialization, or reinitialization of the filter by the transmission of actual signal values $f_n$ thereto. It here will be noted, that at the start of operation, the reconstruction filter poles are momentarily moved inwardly of the unit circle to avoid generation of a random ramp function at the output therefrom.

Obviously, the invention is not limited to inward movement of reconstruction filter poles to a single location in the presence of an error signal. Several values of m may be employed, with filter operation being stepped through several different pole locations during recovery from bit errors. For example, values of m equal 2, 4, and 7 may be used wherein operation first is switched to m equals 2, then m equals 4, and finally to m equals 7, before stepping back to the original value of m, either on, or inside, the unit circle in the Z-plane.

The invention having been described in detail in accordance with requirements of the Patent Statutes, various other changes and modifications will suggest themselves to those skiiled in this art. For example, many of the illustrated functions may be implemented using a digital computer with suitable computer routines. It is intended that this and other such changes and modifications shall fall within the spirit and scope of the invention defined in the appended claims.

I claim:

1. In a data compression system for handling a stream of digital sample signals, the combination comprising, digital compression filter means responsive to the digital sample signals for generating a stream of compressed signals, the transfer function in the Z-plane of the digital compression filter having zeros on the unit circle,
digital reconstruction filter means having a transfer function in the Z-plane with poles normally on or inside the unit circle at the same angular positions as the zeros of the digital compression filter means,
means for transferring the output from the digital compression filter means to the digital reconstruction filter means, and
means responsive to transient errors in the transfer of the output from the digital compression filter means to the digital reconstruction filter means for momentarily moving the poles of the reconstruction filter means inwardly of the unit circle in the Z-plane from their normal positions without changing the angular positions thereof to facilitate recovery from transient errors.

2. In a data compression system as defined in claim 1 wherein the poles of the reconstruction filter are moved inwardly for substantially 50 ms by said means for momentarily moving the poles in response to transient errors.

3. In a data compression system as defined in claim 1 wherein the poles of the reconstruction filter return to normal pole positions in steps following inward movement of the poles in response to transient errors.

4. In a data compression system as defined in claim 1 wherein the poles of the reconstruction filter normally are on the unit circle in the Z-plane.

5. In a data compression system as defined in claim 1 wherein the poles of the reconstruction filter normally are inside the unit circle in the Z-plane.

6. A method of compression and reconstruction filtering a stream of digital sample signals comprising,
obtaining a stream of compressed signals by compression filtering the stream of digital sample signals by a digital compression filter,
operating the compression filter with a transfer function in the Z-plane having zeros on the unit circle,
transferring the compressed signals to reconstruction filter means for reconstruction filtering of the compressed signal stream,
normally operating the reconstruction filter means with a transfer function in the Z-plane having poles on or inside the unit circle at the same angular positions as said zeros,
sensing transient errors in the transfer of compressed signals to the reconstruction filter means, and
in response to sensed transient errors, momentarily moving the poles of the reconstruction filter means inwardly without changing the angular position thereof to facilitate recovery from said transient errors.

7. A method as defined in claim 6 wherein the reconstruction filter means normally is operated to provide a transfer function in the Z-plane having poles on the unit circle, which poles are momentarily moved inside the unit circle in response to transient errors.

8. A method as defined in claim 7 which includes moving the poles of the reconstruction filter means in the Z-plane in steps when returning from the moved to the normal pole positions.

9. A method as defined in claim 6 wherein the reconstruction filter means normally is operated to provide a transfer function in the Z-plane having poles inside the unit circle, which poles are momentarily moved further inside the unit circle in response to transient errors.

10. A method as defined in claim 9 which includes moving the poles of the reconstruction filter means in the Z-plane in steps when returning from the moved to the normal pole positions.

11. A method as defined in claim 6 wherein the poles of the reconstruction filter are moved from the normal to the moved positions for substantially 50 ms in response to transient errors.

* * * * *